United States Patent
Stephens et al.

(10) Patent No.: US 10,047,359 B2
(45) Date of Patent: Aug. 14, 2018

(54) METHODS FOR PRODUCING STRANDED CDNA LIBRARIES

(71) Applicant: Illumina, Inc., San Diego, CA (US)

(72) Inventors: Kathryn M. Stephens, Poway, CA (US); Marcus Burch, Lake Villa, IL (US)

(73) Assignee: ILLUMINA, INC., San Diego, CA (US)

(*) Notice: Subject to any disclaimer, the term of this patent is extended or adjusted under 35 U.S.C. 154(b) by 281 days.

(21) Appl. No.: 14/993,908

(22) Filed: Jan. 12, 2016

(65) Prior Publication Data
US 2016/0194628 A1 Jul. 7, 2016

Related U.S. Application Data

(62) Division of application No. 13/835,757, filed on Mar. 15, 2013, now Pat. No. 9,255,265.

(51) Int. Cl.
- *C12Q 1/68* (2018.01)
- *C12P 19/34* (2006.01)
- *C12N 15/10* (2006.01)

(52) U.S. Cl.
CPC ..... *C12N 15/1065* (2013.01); *C12N 15/1093* (2013.01); *C12N 15/1096* (2013.01)

(58) Field of Classification Search
None
See application file for complete search history.

(56) References Cited

U.S. PATENT DOCUMENTS

| | | | |
|---|---|---|---|
| 4,675,285 A | 6/1987 | Clark et al. | |
| 4,683,195 A | 7/1987 | Mullis et al. | |
| 4,889,818 A | 12/1989 | Gelfand et al. | |
| 4,971,903 A | 11/1990 | Hyman et al. | |
| 5,066,584 A | 11/1991 | Gyllensten et al. | |
| 5,093,245 A | 3/1992 | Keith et al. | |
| 5,130,238 A | 7/1992 | Malek et al. | |
| 5,409,818 A | 4/1995 | Davey et al. | |
| 5,455,166 A | 10/1995 | Walker et al. | |
| 5,508,169 A | 4/1996 | Deugau et al. | |
| 5,641,658 A | 6/1997 | Adams et al. | |
| 6,060,288 A | 5/2000 | Adams et al. | |
| 6,090,592 A | 7/2000 | Adams et al. | |
| 6,107,023 A | 8/2000 | Reyes et al. | |
| 6,175,002 B1 | 1/2001 | DuBridge et al. | |
| 6,300,070 B1 | 10/2001 | Boles et al. | |
| 6,468,751 B1 | 10/2002 | Adams et al. | |

(Continued)

FOREIGN PATENT DOCUMENTS

| EP | 0 224 126 A2 | 6/1987 |
|---|---|---|
| EP | 0 372 524 A2 | 6/1990 |

(Continued)

OTHER PUBLICATIONS

Akowitz et al., "A novel cDNA/PCR strategy for efficient cloning of small amounts of undefined RNA," *Gene*, 81(2):295-306 (1989).

(Continued)

*Primary Examiner* — Young J Kim
(74) *Attorney, Agent, or Firm* — Illumina, Inc.

(57) ABSTRACT

The present system provides novel methods and compositions for selecting a particular strand of RNA and/or producing a cDNA library that results in an unbiased representation of RNA in a sample.

12 Claims, 6 Drawing Sheets

(56) References Cited

U.S. PATENT DOCUMENTS

| | | | |
|---|---|---|---|
| 7,037,687 | B2 | 5/2006 | Williams et al. |
| 7,115,400 | B1 | 10/2006 | Adessi et al. |
| 7,414,166 | B2 | 8/2008 | Beech et al. |
| 7,427,673 | B2 | 9/2008 | Balasubramanian et al. |
| 7,772,384 | B2 | 8/2010 | Balasubramanian et al. |
| 7,795,424 | B2 | 9/2010 | Liu et al. |
| 7,960,120 | B2 | 6/2011 | Rigatti et al. |
| 7,972,820 | B2 | 7/2011 | Mayer et al. |
| 7,985,565 | B2 | 7/2011 | Kawashima et al. |
| 8,084,590 | B2 | 12/2011 | Liu et al. |
| 8,143,008 | B2 | 3/2012 | Kawashima et al. |
| 8,158,346 | B2 | 4/2012 | Balasubramanian et al. |
| 8,192,930 | B2 | 6/2012 | Vermaas et al. |
| 9,255,265 | B2 * | 2/2016 | Stephens ............ C12N 15/1093 |
| 2005/0153333 | A1 * | 7/2005 | Sooknanan ........ C12N 15/1096 435/6.12 |
| 2011/0189679 | A1 | 8/2011 | Kurn et al. |
| 2012/0010091 | A1 | 1/2012 | Linnarson |
| 2012/0237943 | A1 | 9/2012 | Soldatov et al. |
| 2012/0258455 | A1 | 10/2012 | Behlke et al. |

FOREIGN PATENT DOCUMENTS

| | | | |
|---|---|---|---|
| EP | 2 272 976 | 1/2011 | |
| WO | WO 1988/010315 A1 | 12/1988 | |
| WO | WO 1996/04404 | 2/1996 | |
| WO | WO 1998/44151 | 10/1998 | |
| WO | WO-0136680 A2 * | 5/2001 | ........... C12Q 1/6855 |
| WO | WO 2004/081183 A2 | 9/2004 | |
| WO | WO 2007/010251 | 1/2007 | |
| WO | 2007/062495 A1 | 6/2007 | |
| WO | WO 2007/102006 A2 | 9/2007 | |
| WO | WO 2011/003630 A1 | 1/2011 | |
| WO | WO 2011/100569 | 8/2011 | |
| WO | WO 2011/151777 | 12/2011 | |

OTHER PUBLICATIONS

Anderson et al., "A short primer for sequencing DNA cloned in the single-stranded phage vector M13mp2," Nucleic Acids Res., 8(8):1731-1743 (1980).

Armour et al., "Digital transcriptome profiling using selective hexamer priming for cDNA synthesis," Nature Methods, 6(9): 647-650 (2009).

Borodina et al., "A Strand-Specific Library Preparation Protocol for RNA Sequencing," Methods in Enzymology, 500:79-98 (2011).

Church et al., "Multiplex DNA sequencing," Science, 240(4849):185-188 (1988).

Church, "G. Preliminary Results," Annual Technical Progress Report, Accession No. DE91013887, pp. 15-19 (1988).

Comb et al., "Partial characterization of the mRNA that codes for enkephalins in bovine adrenal medulla and human pheochromocytoma," Proc. Natl. Acad. Sci., USA, 79:360-364 (1982).

Duchene et al., "Sequence and transcriptional start site of the Pseudomonas aeruginosa outer membrane porin protein F gene," J. Bacteriol. 170(1):155-162 (1988).

Epicentre, Scientific Posters, "Indicating a Date for Sooknanan Poster Presentation, 2011," Annual Advances in Genome Biology and Technology (AGBT) Meeting, 2011 (1 page).

Erlich, "Part Two, Research Applications," PCR Technology Principles and Applications for DNA Amplification, Stockton Press, United States, pp. 39-43 (1989).

Gardner et al., "The complete nucleotide sequence of an infectious clone of cauliflower mosaic virus by M13mp7 shotgun sequencing," Nucleic Acids Res., 9(12):2871-2888 (1981).

Genomic DNA Sample Prep Kits, [online]. Illumina, Inc., [retrieved on Jan. 16, 2010]. Retrieved from the internet: <URL:www.illumina.com/products/genomic_dna_sample_prep_kits.ilmn.

Helfman et al., "Directional cDNA cloning in plasmid vectors by sequential addition of oligonucleotide linkers," Methods in Enzymology 152:349-359 (1987).

Helfman et al., "Identification of clones that encode chicken tropomyosin by direct immunological screening of a cDNA expression library," Proc. Natl. Acad. Sci., USA, 80:31-35 (1983).

Hoen, et al., "Deep sequencing-based expression analysis shows major advances in robustness, resolution and inter-lab portability over five microanny platforms", Nucleic Acids Research, 1-12 (2008).

Hoen, et al., Supplementary Information for "Deep sequencing-based expression analysis shows major advances in robustness, resolution and inter-lab portability over five microarray platforms", Figures 1-9, 11 pages (2008).

Hultman et al., "Direct solid phase sequencing of genomic and plasmid DNA using magnetic beads as solid support," Nucleic Acids Res., 17(13):4937-4946 (1989).

Huynh et al., "Constructing and Screening cDNA libraries in ηgt10 and ηgt11," in DNA Cloning: A Practical Approach, vol. 1 (Glover, D. M., ed.), IRL, Oxford, UK, pp. 49-78 (1985).

Hyman E. D. , "A New Method of Sequencing DNA," Analytical Biochemistry, 174:423-436 (1988).

Illumina Sequencing Technology, Technology Spotlight: Illumina® Sequencing, Pub. No. 770-2007-002, Oct. 8, 2008.

Illumina, Inc., "Preparing Samples for Digital Gene Expression-Tag Profiling with Rpnll," 1-26 (2007).

Illumina, Inc., "Small RNA v1.5 Sample Preparation Guide", For Research Use Only, Sep. 2010, 1-32.

Illumina, Inc., "TrueSeq RNA and DNA Sample Preparation Kits v2", For Research Use Only, Apr. 27, 2011, 1-4.

Introduction to the Genome Analyzer, Illumina, Inc., pp. 1-70 (2006).

Johnson, "Molecular cloning of DNA from specific chromosomal regions by microdissection and sequence-independent amplification of DNA," Genomics, 6:243-251 (1990).

Kempe et al., "Chemical and enzymatic biotin-labeling of oligodeoxyribonucleotides," Nucleic Acids Res., 13(1):45-59 (1985).

Kimmel et al., "Preparation of cDNA and the generation of cDNA libraries: overview," Methods in Enzymology, 152:307-316 (1987).

Kinzler et al., "Whole genome PCR: application to the identification of sequences bound by gene regulatory proteins," Nucleic Acids Res., 17(10):3645-3653 (1989).

Lawyer et al., "High-level Expression, Purification, and Enzymatic Characterization of Full-length Thermus aquaticus DNA Polymerase and a Truncated From Deficient in 5' to 3' Exonuclease Activity," PCR Meth. Appl., 2:275-287 (1993).

Lawyer et al., "Isolation, Characterization, and Expression iEnscherichia coli of the DNA Polymerase Gene from Thermus aquaticus," J. Biol. Chem., 264:6427-6437 (1989).

Levin et al., "Comprehensive comparative analysis of strand-specific RNA sequencing methods," Nature Methods, 7(9): 709-718 (2010).

Lewin, "National academy looks at human genome project, sees progress," Science, 235:747-748 (1987).

Lewis et al., "Detection of proopiomelanocortin mRNA by in situ hybridization with an oligonucleotide probe," Proc. Natl. Acad. Sci. USA, 83:5419-5423 (1986).

Liang et al., "Rapid plasmid insert amplification with polymerase chain reaction," Nucleic Acids Res. 16(8):3579 (1988).

Lucito et al., "Genetic analysis using genomic representations," Proc. Natl. Acad. Sci., USA 95:4487-4492 (1998).

Mamanova et al., "FRT-seq: amplification-free, strand-specific transcriptome sequencing," Nature Methods, 7(2): 130-134 (2010).

Metzger, M. L., et al. "Termination of DNA synthesis by novel 3'-modifieddeoxyribonucleoside 5'-triphosphates ," Nucleic Acids Research, 22:4259-4267 (1994).

Mullis et al., "Specific synthesis of DNA in vitro via a polymerase-catalyzed chain reaction," Methods in Enzymology 155:335-350 (1987).

Parkhomchuk et al., "Transcriptome analysis by strand-specific sequencing of complementary DNA," Nucleic Acids Research, 37(18):1-7 (2009).

Reyes et al., "Isolation of cDNA from the virus responsible for enterically transmitted non-A, non-B hepatitis," Science, 247:1335-1339 (1990).

(56) References Cited

OTHER PUBLICATIONS

Reyes et al., "Sequence-idependent, single-primer amplification (SISPA) of complex DNA populations," *Mol. Cell. Probes*, 5:473-481 (1991).

Ronaghi et al., "A Sequencing Method Based on Real-Time Pyrophosphate," Science 281:363-365 (1998).

Rosenthal et al., "Genomic walking and sequencing by oligo-cassette mediated polymerase chain reaction," *Nucleic Acids Res.*, 18(10):3095-3096 (1990).

Saiki et al., "Enzymatic amplification of β-globin genomic sequences and restriction site analysis for diagnosis of sickle cell anemia," *Science* 230:1350-1354 (1985).

Saiki et al., "Primer-directed enzymatic amplification of DNA with a thermostable DNA polymerase," *Science*, 239:487-491 (1988).

Saltman et al., "Isolation of region-specific cosmids from chromosome 5 by hybridization with microdissection clones," *Nucleic Acids Res.* 20(6):1401-1404 (1992).

Saltzgaber-Muller et al., "Detection of corynebacterium kutscheri in animal tissues by DNA-DNA hybridization," *J. Clin. Microbiol.*, 24(5):759-763 (1986).

Saunders et al., "PCR amplification of DNA microdissected from a single polytene chromosome band: a comparison with conventional microcloning," *Nucleic Acids Res.*, 17(22):9027-9037 (1989).

Sherry et al., "Resolution of the two components of macrophage inflammatory protein 1, and cloning and characterization of one of those components, macrophage inflammatory protein 1β," *J. Exp. Med.*, 168:2251-2259 (1988).

Sooknanan et al., "Improved Technologies for Ribosomal RNA Removal and Directional RNA-Seq. Library Preparation," Poster, 2011 Annual Advances in Genome Biology and Technology (AGBT) Meeting, Floriday, Feb. 2-5, 2011 (1 page).

Sooknanan et al., Nucleic Acid Sequence-Based Amplification, Ch. 12 (pp. 261-285) of Molecular Methods for Virus Detection, Academic Press, (1995).

Soreq, Report No. 4, Molecular Cloning of Human Gene(s) Directing the Synthesis of Nervous System Cholinesterases, Sep. 1987.

Stehelin et al., "DNA related to the transforming gene(s) of avian sarcoma viruses is present in normal avian DNA," *Nature*, 260:170-173 (1976).

Stein et al., "Oligonucleotides as inhibitors of gene expression: a review," *Cancer Res.*, 48:2659-2668 (1988).

Welcher et al., "Selective enrichment of specific DNA, cDNA and RNA sequences using biotinylated probes, avidin and copper-chelate agarose," *Nucleic Acids Res.*, 14(24):10027-10044 (1986).

Westin et al., "OVEC, a versatile system to study transcription in mammalian cells and cell-free extracts," *Nucleic Acids Res.*, 15(17):6787-6798 (1987).

Wu et al., "Adaptors, Linkers, and Methylation," *Methods in Enzymology*, 152:343-349 (1987).

Zhou, et al., "Closed-Tube Genotyping with Unlabeled Oligonucleotide Probes and a Saturating DNA Dye," Clin. Chem., 50: 1328-1335 (2004).

Patent Cooperation Treaty, International Search Report and Written Opinion, for PCT Appln. No. PCT/US2014/023257, dated Jul. 21, 2014, 15 pages.

* cited by examiner

METHODS FOR PRODUCING STRANDED CDNA LIBRARIES

CROSS-REFERENCE TO RELATED APPLICATIONS

This application is a divisional of U.S. application Ser. No. 13/835,757, filed Mar. 15, 2013, the entire contents of which is incorporated herein by reference.

BACKGROUND OF THE INVENTION

The present invention relates generally to methods for generated stranded cDNA libraries.

As the complexities of gene regulation become better understood, a need for capturing additional data has emerged. Stranded information identifies from which of the two DNA strands a given RNA transcript was derived. This information can provide, for example, increased confidence in transcript annotation, transcript discovery and expression profiling. Additionally, identifying strand origin can increase the percentage of alignable reads, thereby reducing sequencing cost per sample. Maintaining strand orientation also allows identification of antisense expression, which is an important mediator of gene regulation. The ability to capture the reactive abundance of sense and antisense expression provides visibility to regulator interactions that might otherwise be missed.

Methods for determining mRNA sequences can involve analyzing the DNA sequence of single clones of a cDNA library, which can be derived by enzymatic production of double-stranded cDNA from the mRNA isolated from a target cell or population of cells. Methods for determining the relative abundance of mRNA species typically involve quantifying the hybridization of a defined nucleic acid sequence to a complementary sequence in the mRNA population. Analysis of samples containing a relatively low quantity of mRNA can involve amplification prior to the application of methods for determining the sequence or relative abundance, of particular mRNA species. One of ordinary skill also recognizes that amplification methods that proceed exponentially are more likely to introduce bias in the relative levels of different mRNAs.

Existing methods developed for amplification of nucleic acid molecules have their shortcomings. Some methods suffer from, for example, sequence bias during exponential amplification and inefficiency of single-stranded ligation, the narrow applicability to a few forms of RNA and DNA, and the requirement of a 5'-terminal CAP. Accordingly, there exists a need for methods that are capable of unbiased selection of stranded RNA sequences from an RNA sample. The present invention satisfies this need and provides related advantages.

SUMMARY OF INVENTION

As described herein, the present system provides novel methods and compositions for selecting a particular strand of RNA and/or producing a cDNA library that results in an unbiased representation of RNA in a sample. In some embodiments, the methods of the system include use of two specific polynucleotide adapters. In some aspects, the first polynucleotide comprises a polynucleotide primer that has a random nucleotide sequence on its 3' end and a first nucleotide sequence tag. The second polynucleotide can be a double-stranded polynucleotide adapter comprising a second nucleotide sequence tag and either 3' overhand or a blunt end. In some embodiments, when the double-stranded polynucleotide having a 3' overhang is used, the 3' overhang includes a second random nucleotide sequence and in some aspects a 3' block.

Accordingly, the system provides a method for selecting a particular strand of an RNA molecule in an RNA sample including one or more of the steps of: hybridizing a first primer to an RNA sample under conditions wherein a complex is formed between a 3' region of the first primer and an RNA molecule in the RNA sample, wherein the 3' region of the first primer includes a first random nucleotide sequence and a first nucleotide sequence tag; extending the first primer by reverse transcription or a comparable enzyme or method known in the art, thereby generating a complementary molecule (e.g. a cDNA molecule); hybridizing a double stranded polynucleotide molecule including a second nucleotide sequence tag to the complementary molecule under conditions wherein: (i) a complex is formed between a 3' overhang of the double stranded polynucleotide molecule and a 3' region of the cDNA molecule, wherein the 3' overhang includes a second random nucleotide sequence, and (ii) a 5' end of a complementary second strand of the double stranded polynucleotide molecule is adjacent to a 3' end of the complementary molecule; attaching the 5' end of the complementary second strand of the double stranded polynucleotide molecule to the 3' end of the cDNA molecule, thereby generating an unattached strand of the double stranded polynucleotide molecule. The method can also include removing the unattached strand of the double stranded polynucleotide molecule and/or selecting for a particular cDNA strand of the RNA molecule.

In another embodiment, the system provides a method for selecting a particular strand of an RNA molecule in an RNA sample including one or more of the steps of: hybridizing a first primer to an RNA sample under conditions wherein a complex is formed between a 3' region of the first primer and an RNA molecule in the RNA sample, wherein the 3' region of the first primer includes a random nucleotide sequence and a first nucleotide sequence tag; extending the primer of the complex by reverse transcription or a comparable enzyme or method known in the art, thereby generating a complementary strand (e.g. cDNA) of the RNA molecule; attaching a double stranded polynucleotide molecule to the complementary strand, and wherein the double stranded polynucleotide molecule includes a second nucleotide sequence tag. Attaching the double stranded polynucleotide molecule to the complementary strand can be done under conditions wherein the RNA molecule is less efficiently attached to the double stranded polynucleotide molecule (e.g. not attached or attached to a lesser extent that the complementary strand). Particularly when the RNA strand is not attached, the method may also include extending the unattached strand of the double stranded DNA molecule. The method also can include selecting for the particular cDNA strand of the RNA molecule.

In one embodiment, the system provides a method for creating a cDNA library representing a particular strand of a RNA molecule in an RNA sample. The method can include one or more of: hybridizing a plurality of first primers to an RNA sample under conditions wherein complexes are formed between a 3' region of two or more first primers in the plurality of first primers and two or more RNA molecules in the RNA sample, wherein the 3' region of the first primers include a random nucleotide sequence and a first nucleotide sequence tag; extending the plurality of first primers of the complexes by reverse transcription or a comparable enzyme or method known in the art, thereby generating a complementary strand (e.g. cDNA) of the two or more RNA molecules; hybridizing a plurality of double stranded polynucleotide molecules including a second nucleotide sequence tag to the two or more complementary strands under conditions wherein: (i) a complex is formed between a 3' overhang of a double stranded polynucleotide molecule in the plurality of double stranded polynucleotide molecules and a 3' region of the complementary strand, wherein the 3' overhang includes a second random nucleotide sequence, and (ii) a 5' end of a complementary second strand of the double stranded polynucleotide molecule in the plurality of double stranded polynucleotide molecules is adjacent to a 3' end of the complementary strand; attaching the 5' end of the complementary second strand of the double stranded polynucleotide molecule to the 3' end of the two or more complementary strands, thereby generating unattached strands of the double stranded polynucleotide molecules; removing the unattached strands the double stranded polynucleotide molecules, thereby forming a plurality of single stranded complementary strands including a first and a second nucleotide sequence tag; and converting the plurality of single stranded complementary stands to double stranded cDNA molecules, thereby creating a cDNA library representing a particular strand of a RNA molecule of in an RNA sample.

In another embodiment, the system provides a method for creating a cDNA library representing a particular strand of a RNA molecule in an RNA sample, wherein the method includes one or more of the steps of: hybridizing a plurality of first primers to an RNA sample under conditions wherein complexes are formed between a 3' region of two or more first primers in the plurality of first primers and two or more RNA molecules in the RNA sample, wherein the 3' region of the single stranded primers include a random nucleotide sequence and a first nucleotide sequence tag; extending the first primers of the complexes by reverse transcription or a comparable enzyme or method known in the art, thereby generating a complementary strand (e.g. cDNA) of the two or more RNA molecules; attaching double stranded polynucleotide molecules to the complementary strands under conditions wherein the RNA molecules are not attached to the double stranded DNA molecules, wherein the double stranded DNA molecules include a second nucleotide sequence tag; and extending the unattached strand of the double stranded DNA molecules, thereby forming a cDNA library representing a particular strand of an RNA molecule in an RNA sample.

In one embodiment, the system also provides a cDNA library produced using any one of the methods disclosed herein.

DETAILED DESCRIPTION OF THE INVENTION

Figure 1A:
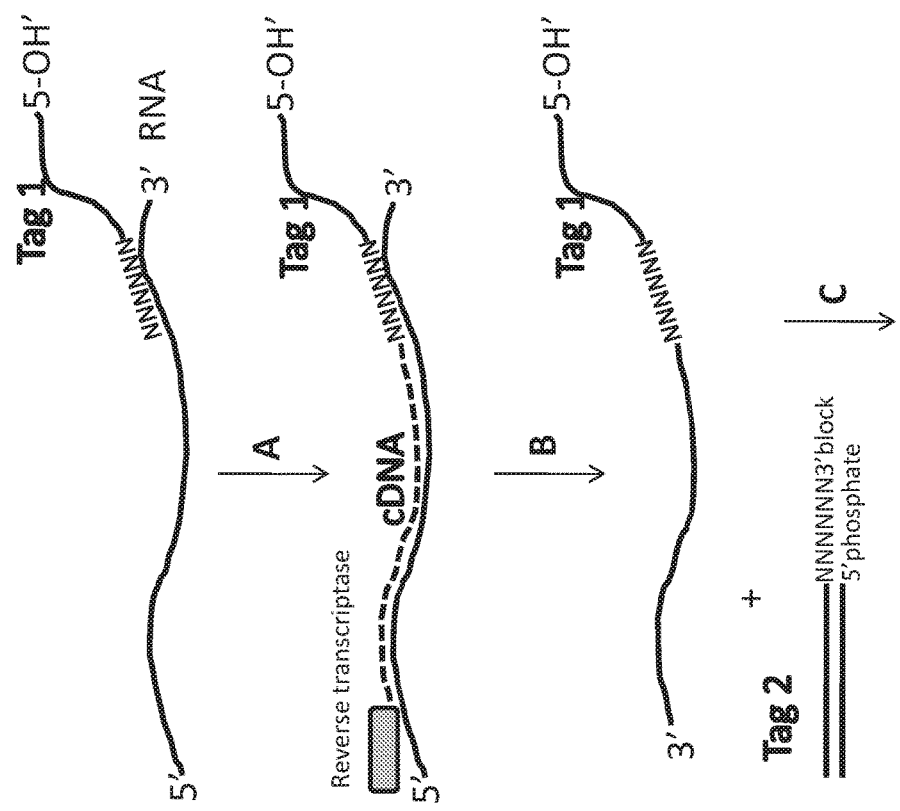
FIGS. 1A and 1B shows a schematic illustration of Method A of the system.

The term "polynucleotide" refers to a polymeric form of nucleotides of any length, including deoxyribonucleotides and/or ribonucleotides, or analogs thereof. Polynucleotides can have any three-dimensional structure and may perform any function, known or unknown. The structure of a polynucleotide can also be referenced to by its 5' or 3' end or terminus, which indicates the directionality of the polynucleotide. Adjacent nucleotides in a single-strand of polynucleotides are typically joined by a phosphodiester bond between their 3' and 5' carbons. However, different internucleotide linkages could also be used, such as linkages that include a methylene, phosphoramidate linkages, etc. This means that the respective 5' and 3' carbons can be exposed at either end of the polynucleotide, which may be called the 5' and 3' ends or termini. The 5' and 3' ends can also be called the phosphoryl ($PO_4$) and hydroxyl (OH) ends, respectively, because of the chemical groups attached to those ends. The term polynucleotide also refers to both double- and single-stranded molecules. Unless otherwise specified or required, any embodiment that makes or uses a polynucleotide encompasses both the double-stranded form and each of two complementary single-stranded forms known or predicted to make up the double-stranded form. The following are non-limiting examples of polynucleotides: a gene or gene fragment (for example, a probe, primer, EST or SAGE tag), genomic DNA, genomic DNA fragment, exon, intron, messenger RNA (mRNA), transfer RNA, ribosomal RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can include modified nucleotides, such as methylated nucleotides and nucleotide analogs (including nucleotides with non-natural bases, nuculeotides with modified natural bases such as aza- or deaza-purines, etc.). If present, modifications to the nucleotide structure can be imparted before or after assembly of the polynucleotide. A polynucleotide can also be further modified after polymerization, such as by conjugation with a labeling component. Additionally, the sequence of nucleotides in a polynucleotide can be interrupted by non-nucleotide components. One or more ends of the polynucleotide can be protected or otherwise modified to prevent that end from interacting in a particular way (e.g. forming a covalent bond) with other polynucleotides.

A polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term "sequence" refers to the alphabetical representation of a polynucleotide or any nucleic acid molecule, including natural and non-natural bases.

The term "RNA molecule" or ribonucleic acid molecule refers to a polynucleotide having a ribose sugar rather than deoxyribose sugar and typically uracil rather than thymine as one of the pyrimidine bases. An RNA molecule of the invention is generally single-stranded, but can also be double-stranded. In the context of an RNA molecule from an RNA sample, the RNA molecule can include the single-stranded molecules transcribed from DNA in the cell nucleus, mitochondrion or chloroplast, which have a linear sequence of nucleotide bases that is complementary to the DNA strand from which it is transcribed.

The term "hybridization," "hybridizing" or grammatical equivalent thereof, refers to a reaction in which one or more polynucleotides react to form a complex that is formed at least in part (typically stabilized) via hydrogen bonding between the bases of the nucleotide residues. The hydrogen bonding can occur by Watson-Crick base pairing, Hoogstein binding, or in any other sequence-specific manner. The complex can have two strands forming a duplex structure, three or more strands forming a multi-stranded complex, a single self-hybridizing strand, or any combination of thereof. The strands can also be cross-linked or otherwise joined by forces in addition to hydrogen bonding.

A "primer" refers to a short polynucleotide, generally with a free 3'-OH group, that binds to a target or template polynucleotide present in a sample by hybridizing with the target or template, and thereafter promoting extension of the primer to form a polynucleotide complementary to the target or template. For example, a polymerase chain reaction (PCR) is a reaction in which replicate copies are made of a target polynucleotide using a pair of primers or a set of primers consisting of an upstream and a downstream primer, and a catalyst of polymerization, such as a DNA polymerase. As another example, primers may be used in an isothermal amplification process such as self-sustain sequence replication based amplification and/or bridge amplification. Primers of the instant invention can include polynucleotides ranging from 10 to 1000 or more nucleotides. In one aspect, the primer is at least 10 nucleotides, or alternatively, at least 15 nucleotides, or alternatively, at least 20 nucleotides, or alternatively, at least 20 nucleotides, or alternatively, at least 30 nucleotides, or alternatively, at least 40 nucleotides, or alternatively, at least 50 nucleotides, or alternatively, at least 60 nucleotides, or alternatively, at least 70 nucleotides, or alternatively, at least 80 nucleotides, or alternatively, at least 90 nucleotides, or alternatively, at least 100 nucleotides, or alternatively, at least 200 nucleotides, or alternatively, at least 300 nucleotides, or alternatively at least 400 nucleotides, or alternatively at least 500 nucleotides or alternatively at least 1000 nucleotides. In one aspect, the primer is no more than 10 nucleotides, or alternatively, no more than 15 nucleotides, or alternatively, no more than 20 nucleotides, or alternatively, no more than 20 nucleotides, or alternatively, no more than 30 nucleotides, or alternatively, no more than 40 nucleotides, or alternatively, no more than 50 nucleotides, or alternatively, no more than 60 nucleotides, or alternatively, no more than 70 nucleotides, or alternatively, no more than 80 nucleotides, or alternatively, no more than 90 nucleotides, or alternatively, no more than 100 nucleotides, or alternatively, no more than 200 nucleotides, or alternatively, no more than 300 nucleotides, or alternatively no more than 400 nucleotides, or alternatively no more than 500 nucleotides or alternatively no more than 1000 nucleotides.

A "probe" when used in the context of polynucleotide manipulation refers to an polynucleotide that is provided as a reagent to detect or immobilize a target potentially present in a sample of interest by hybridizing with the target bearing a complementary nucleotide sequence. A probe may be a unique probe that essentially uniquely pulls out a particular target or small subset of targets, or a probe may be a non-unique probe that has the potential to pull out multiple different polynucleotides from a particular sample. Polynucleotide probes of the invention range in length from about 10 to 5,000 nucleotides. In one aspect, the probe is at least 10 nucleotides, or alternatively, at least 20 nucleotides, or alternatively, at least 30 nucleotides or alternatively, at least 50 nucleotides, or alternatively, at least 75, or alternatively, at least 100 nucleotides, or alternatively, at least 200 nucleotides, or alternatively, at least 500 nucleotides, or alternatively, at least 1000 nucleotides, or alternatively, at least 2000 nucleotides, or alternatively, at least 3000 nucleotides, or alternatively, at least 5000 nucleotides. In one aspect, the probe is no more than 10 nucleotides, or alternatively, no more than 20 nucleotides, or alternatively, no more than 30 nucleotides or alternatively, no more than 50 nucleotides, or alternatively, no more than 75, or alternatively, no more than 100 nucleotides, or alternatively, no more than 200 nucleotides, or alternatively, no more than 500 nucleotides, or alternatively, no more than 1000 nucleotides, or alternatively, no more than 2000 nucleotides, or alternatively, no more than 3000 nucleotides, or alternatively, no more than 5000 nucleotides. A probe can include a detectable label or a modification by which a label can be attached, either before or subsequent to the hybridization reaction.

The phrase "random nucleotide sequence" refers to a varied sequence of nucleotides that when combined with other random nucleotide sequences in a population of polynucleotides represent all or substantially all possible combinations of nucleotides for a given length of nucleotides. For example, because of the four possible nucleotides present at any given position, a sequence of two random nucleotides in length has 16 possible combinations, a sequence of three random nucleotides in length has 64 possible combinations, or a sequence of four random nucleotides in length has 265 possible combination. Accordingly, when used in reference to the methods of the invention, a random nucleotide sequence has the potential to hybridize to any target polynucleotide in the sample.

The "random" sequences described herein may be completely random or may only be partly random (e.g. at least 30%, at least 40%, at least 50%, at least 60%, at least 70%, at least 80%, and/or at least 90% of the base positions in the "random" portion of the polynucleotide are random). A random sequence at a particular base position can be provided by including a plurality of probes that have at least two, three, or four different versions where each version has a different base at that position (i.e. full or partially degenerate set of probes for that position), and/or may include a base such as inosine which hybridizes with more than one (e.g. two, three, four, etc.) different types of bases.

The phrase "sequence tag" refers to a nucleotide sequence that is attached to a primer or probe, or incorporated into a polynucleotide, that allows for the identification, tracking, or isolation of the attached primer, probe or polynucleotide in a subsequent reaction or step in a method or process. Thus, a sequence tag can be non-native to the target sequence, i.e. is exogenous. It should be noted that in this context, the target sequence can include the primary sample target sequence of the RNA in the sample, or can be a derivative target such as a reactant or product of the reactions outlined herein. Thus, for example, the target sequence can be a cDNA product produced by reverse transcription, a ligation product, a PCR product, etc. The nucleotide composition of a sequence tag can be chosen so as to allow hybridization to a complementary probe on a solid support, such as the surface of an array, or hybridization to a complementary primer used to selectively amplify a target sequence.

The terms "extending," "extension" or any grammatical equivalents thereof refers to the addition of dNTPs to a primer, polynucleotide or other nucleic acid molecule by an extension enzyme such as a polymerase. For example, in some methods disclosed herein, the resulting extended primer includes sequence information of the target RNA. This extended primer can then serve as a template in subsequent specificity steps to identify the target RNA by selecting a specific nucleotide sequence. While some methods are discussed as performing extension using a polymerase (e.g. a DNA polymerase, an RNA polymerase, or a reverse transcriptase), extension can be performed in any other manner well known in the art. For example, extension can be performed by ligating short pieces of random oligonucleotides together (e.g. that have hybridized to the strand of interest). In this case as well as others, the orientations recited (i.e. 5' end and 3' end) in the present application could be the same or could be reversed and are equally contemplated.

The term "synthesizing" when used in the context of generating an polynucleotide such as DNA, refers to the linking together of nucleotides to form the polynucleotide. Synthesis can include extending a probe or primer that is hybridized to a target polynucleotide, wherein the nucleotide sequence of the complementary second strand of polynucleotides is dependent upon the nucleotide sequence of the target polynucleotide. Synthesis can also include the hybridization and extension of a probe or primer, wherein the nucleotide sequence of the resulting polynucleotide is dependent upon the nucleotide sequence of the target polynucleotide.

The phrase "reverse transcription" refers to the process of copying the nucleotide sequence of a RNA molecule into a DNA molecule. Reverse transcription can be done by reacting an RNA template with a RNA-dependent DNA polymerase (also known as a reverse transcriptase) under well known conditions. A reverse transcriptase is a DNA polymerase that transcribes single-stranded RNA into single stranded DNA. Depending on the polymerase used, the reverse transcriptase can also have RNase H activity for subsequent degradation of the RNA template.

The phrase "complementary DNA" or "cDNA" refers to a synthetic DNA reverse transcribed from RNA through the action of a reverse transcriptase. The cDNA may be single stranded or double stranded and can include strands that have either or both of a sequence that is substantially identical to a part of the RNA sequence or a complement to a part of the RNA sequence.

The phrase "cDNA library" refers to a collection of DNA sequences generated from RNA sequences. The cDNA library can represent the RNA present in the original sample from which the RNA was extracted. Accordingly, in some aspects, a cDNA library can represent all or a part of a transcriptome of a given cell or population of cells including messenger RNA (mRNA), ribosomal RNA (rRNA), transfer RNA (tRNA) and other non-coding RNA (ncRNA) produced in one cell or a population of cells.

As used herein, a "3' block" refers to a nucleotide or modified nucleotide, or sequence thereof, that inhibits formation of a subsequent phosphodiester bond between the 3' end of a polynucleotide and another nucleotide. For example, a phosphorylated 3' end of a polynucleotide, which typically has a hydroxyl group on its 3' end, can act as a 3' block because extension by a DNA polymerase would be inhibited or ligation by a ligase would be inhibited. Another non-limiting example of a 3' block includes the addition of a 3' C3 spacer (three-carbon spacer) to the 3' end of a polynucleotide which can function as an effective blocking agent against polymerase extension. Zhou, et al., *Clin. Chem.*, 50: 1328-1335 (2004). Thus, the 3' end of a polynucleotide can be blocked by the addition of, for example, a C3 spacer, a phosphate, an amine group ($NH_2$), or any other chemical modifications that inhibits formation of a subsequent phosphodiester bond between the 3' end of the polynucleotide and another nucleotide.

The term "ligation" or "ligating," or other grammatical equivalents thereof refers to the joining of two nucleotide strands by a phosphodiester bond. Such a reaction can be catalyzed by a ligase. A ligase refers to a class of enzymes that catalyzes this reaction with the hydrolysis of ATP or a similar triphosphate.

As used herein, the term "detectable label" refers to a directly or indirectly detectable compound or composition that is conjugated directly or indirectly to the composition to be detected, e.g., polynucleotide, so as to generate a detectably labeled composition. The term includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, bioluminescent compounds, dyes, and proteins, including enzymes. The label may be simply detected or it may be quantified. A response that is simply detected generally includes a response whose existence merely is confirmed, whereas a response that is quantified generally includes a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally includes a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

By "solid support," "substrate" or other grammatical equivalents herein refers to any material that contains and/or can be modified to contain one or more sites (e.g. discrete individual sites, pre-defined sites, random sites, etc.) appropriate for the attachment or association of compositions disclosed herein and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon. and modified silicon, carbon, metals, inorganic glasses, plastics, optical fiber bundles, and a variety of other polymers. In general, the substrates allow optical detection and do not themselves appreciably fluoresce.

A solid support can be flat (planar), although as will be appreciated by those in the art, other configurations of substrates may be used as well; for example, three dimensional configurations can be used, for example by embedding beads in a porous block of plastic that allows sample access to the beads and using a confocal microscope for detection. Similarly, the beads may be placed on the inside surface of a tube, for flow-through sample analysis to minimize sample volume. In some aspects substrates include optical fiber bundles and flat planar substrates such as glass, polystyrene and other plastics and acrylics. A bead includes a small discrete particle, the composition of which will depend on the class of probe used and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers Ind. is a helpful guide.

The term "phosphorylate" means adding a phosphate group to a molecule, such as polynucleotide. Conversely, the term "dephosphorylate" means removing a phosphate group from a molecule, such as a polynucleotide. In some aspects, phosphorylating or dephosphorylating a polynucleotide refers to the addition or removal of a phosphate group from the 5' or 3' end of the polynucleotide.

As used herein, the term "plurality" is intended to mean a population of two or more different members. Pluralities can range in size from small, medium, large, to very large. The size of small plurality can range, for example, from a few members to tens of members. Medium sized pluralities can range, for example, from tens of members to about 100 members or hundreds of members. Large pluralities can range, for example, from about hundreds of members to about 1000 members, to thousands of members and up to tens of thousands of members. Very large pluralities can range, for example, from tens of thousands of members to about hundreds of thousands, a million, millions, tens of millions and up to or greater than hundreds of millions of members. Therefore, a plurality can range in size from two to well over one hundred million members as well as all sizes, as measured by the number of members, in between and greater than the above exemplary ranges. Exemplary nucleic acid pluralities include, for example, populations of about $1\times10^5$, $5\times10^5$ and $1\times10^6$ or more different nucleic acid species. Accordingly, the definition of the term is intended to include all integer values greater than two. An upper limit of a plurality of the system can be set, for example, by the theoretical diversity of nucleotide sequences in a nucleic acid sample of the system.

As described herein, the present system provides novel methods and compositions for selecting a particular strand of RNA and/or producing a cDNA library that results in an unbiased representation of RNA in a sample. Accordingly, one of ordinary skill in the art would recognize that the products of the methods disclosed herein have a variety of utilities including, without limitation, cloning of known or unknown target nucleic acid molecules, the generation of hybridization probes, the construction of cDNA libraries, and the analysis and identification of nucleotide and amino acid sequences of a target cell or population of cells. For example, when the methods and compositions of the system are combined with well known sequencing techniques, especially high-throughput sequencing techniques, discovery applications include identifying alternative splicing events, gene fusions, allele-specific expression, and examining rare and novel transcripts.

Accordingly, in one embodiment, the system provides a method for selecting a particular strand of an RNA molecule in an RNA sample. In some aspects, the method of the system includes the steps depicted in FIGS. 1A and 1B and described herein as Method A. These steps can include: (a) hybridizing a first primer to an RNA sample under conditions wherein a complex is formed between a 3' region of the first primer and an RNA molecule in the RNA sample, wherein the 3' region of the first primer includes a first random nucleotide sequence and a first nucleotide sequence tag (Tag 1); (b) extending the first primer by reverse transcription, thereby generating a complementary DNA (cDNA) molecule; (c) hybridizing a double stranded polynucleotide molecule including a second nucleotide sequence tag (Tag 2) to the cDNA molecule under conditions wherein: (i) a complex is formed between a 3' overhang of the double stranded polynucleotide molecule and a 3' region of the cDNA molecule, wherein the 3' overhang includes a second random nucleotide sequence, and (ii) a 5' end of a complementary second strand of the double stranded polynucleotide molecule is adjacent to a 3' end of the cDNA molecule; (d) attaching the 5' end of the complementary second strand of the double stranded polynucleotide molecule to the 3' end of the cDNA molecule, thereby generating an unattached strand of the double stranded polynucleotide molecule; (e) removing the unattached strand of the double stranded polynucleotide molecule; and (f) selecting for a particular cDNA strand of the RNA molecule by hybridizing a probe or a second primer to the first or second nucleotide sequence tags.

Figure 2A:
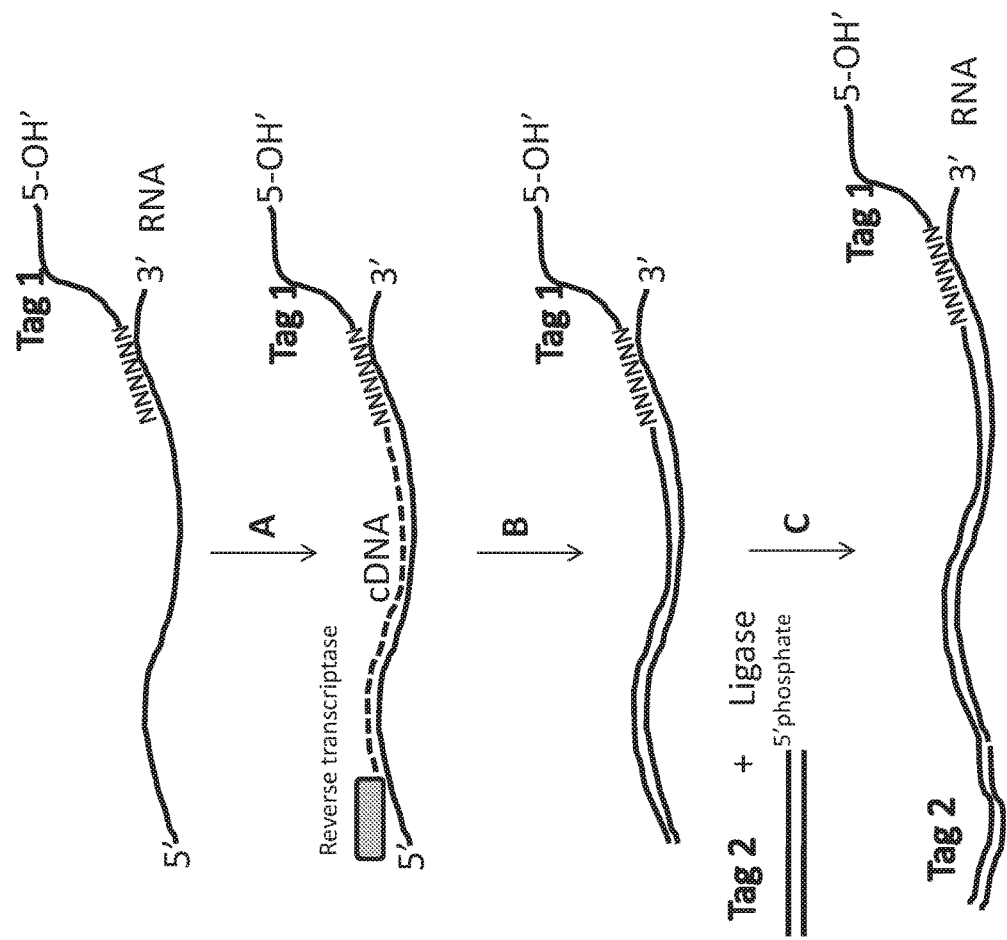
FIGS. 2A and 2B shows a schematic illustration of Method B of the system.
Figure 2B:
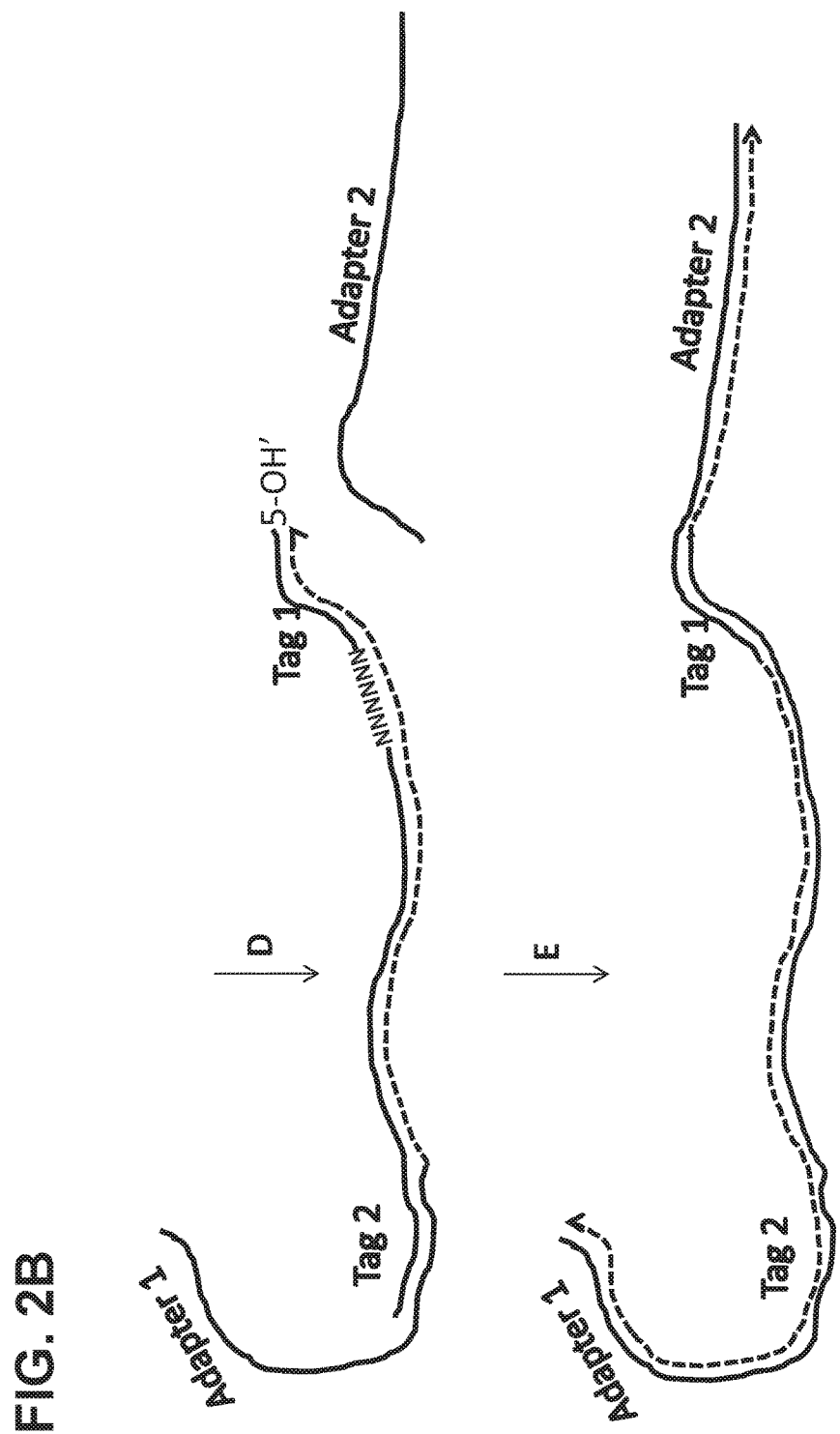

In another embodiment, the system provides a method for selecting a particular strand of an RNA molecule in an RNA sample, wherein the method includes the steps depicted in FIGS. 2A and 2B and described herein as Method B. These steps can include: (a) hybridizing a first primer to an RNA sample under conditions wherein a complex is formed between a 3' region of the first primer and an RNA molecule in the RNA sample, wherein the 3' region of the first primer includes a random nucleotide sequence and a first nucleotide sequence tag (Tag 1); (b) extending the primer of the complex by reverse transcription, thereby generating a complementary DNA (cDNA) molecule of the RNA molecule; (c) attaching a double stranded polynucleotide molecule to the cDNA molecule under conditions wherein the 5' end of the double stranded polynucleotide molecule is attached to the cDNA molecule and the RNA molecule is not attached to the 3' end of the double stranded polynucleotide molecule and wherein the double stranded DNA molecule includes a second nucleotide sequence tag (Tag 2); (d) removing the RNA molecule; and (e) selecting for the particular cDNA strand of the RNA molecule by hybridizing a probe or second primer to the first or second nucleotide sequence tags.

In one embodiment, the system provides a method for creating a cDNA library representing a particular strand of a RNA molecule in an RNA sample. In some aspects, the method includes the steps depicted in FIGS. 1A and 1B, and described herein as Method A. These steps can include: (a) hybridizing a plurality of first primers to an RNA sample under conditions wherein complexes are formed between a 3' region of two or more first primers in the plurality of first primers and two or more RNA molecules in the RNA sample, wherein the 3' region of the first primers include a random nucleotide sequence and a first nucleotide sequence tag; (b) extending the plurality of first primers of the complexes by reverse transcription, thereby generating complementary DNA (cDNA) molecules of the two or more RNA molecules; (c) hybridizing a plurality of double stranded polynucleotide molecules including a second nucleotide sequence tag to the two or more cDNA molecules under conditions wherein: (i) a complex is formed between a 3' overhang of a double stranded polynucleotide molecule in the plurality of double stranded polynucleotide molecules and a 3' region of the cDNA molecule, wherein the 3' overhang includes a second random nucleotide sequence, and (ii) a 5' end of a complementary second strand of the double stranded polynucleotide molecule in the plurality of double stranded polynucleotide molecules is adjacent to a 3' end of the cDNA molecule; (d) attaching the 5' end of the complementary second strand of the double stranded polynucleotide molecule to the 3' end of the two or more cDNA molecules, thereby generating unattached strands of the double stranded polynucleotide molecules; (e) removing the unattached strands the double stranded polynucleotide molecules, thereby forming a plurality of single stranded cDNA molecules including a first and a second nucleotide sequence tag; and (f) converting the plurality of single stranded cDNA molecules to double stranded cDNA molecules, thereby creating a cDNA library representing a particular strand of a RNA molecule of in an RNA sample.

In another embodiment, the system provides a method for creating a cDNA library representing a particular strand of a RNA molecule in an RNA sample, wherein the method includes the steps depicted in FIGS. 2A and 2B, and described herein as Method B. These steps can include: (a) hybridizing a plurality of first primers to an RNA sample under conditions wherein complexes are formed between a 3' region of two or more first primers in the plurality of first primers and two or more RNA molecules in the RNA sample, wherein the 3' region of the single stranded primers include a random nucleotide sequence and a first nucleotide sequence tag; (b) extending the first primers of the complexes by reverse transcription, thereby generating complementary DNA (cDNA) molecules of the two or more RNA molecules; (c) attaching double stranded polynucleotide molecules to the cDNA molecules under conditions wherein the (c) attaching double stranded polynucleotide molecules to the cDNA molecules under conditions wherein the 5' end of the double stranded polynucleotide molecules are attached to the cDNA molecules and the RNA molecules are not attached to the 3' end of the double stranded polynucleotide molecules, wherein the double stranded DNA molecules include a second nucleotide sequence tag; (d) removing said RNA molecules; and (e) synthesizing complementary second strand DNA molecules from said cDNA molecules, thereby forming a cDNA library representing a particular strand of an RNA molecule in an RNA sample.

In one embodiment, the system provides a cDNA library produced using any one of the methods disclosed herein.

The method may also include a step of digesting the RNA (e.g. using RNAse H) before or after the double-stranded polynucleotide molecule is attached.

The method also can include selecting for the particular cDNA strand of the RNA molecule by isolating it from at least some other strands, e.g. by hybridizing a probe or second primer to the first or second nucleotide sequence tags. The particular cDNA strand may also be selected by amplifying the cDNA strand in a manner that enriches the particular cDNA strand compared to at least some other nucleic acids (and in some cases most other and/or at least compared to 30%, or 40% or 50% or 60% or 70% or 80% or 90% of the other strands). Selecting (e.g. isolating and/or enriching) a particular strand may include selecting that strand on its own, or may include selecting that strand simultaneously with selection of other strands (e.g. at least 1000, 10,000, 100,000, or 1,000,000 other strands).

While much of the discussion relates to using primers with a random sequence portion, the method may also be performed using primers that target specific polynucleotides or classes of polynucleotides. For example, the primer may hybridize to the polynucleotide using a non-random sequence (e.g. a poly T or poly A sequence which, in some forms of this embodiment, may end in a random or non-random non-poly-T or non-poly-T sequence that hybridizes with the target). As another example, a primer may include a sequence corresponding to (either substantially complementing or substantially the same as the exon sequence). When multiple polynucleotides are targeted simultaneously, the primers may be the same or different that target the multiple polynucleotides.

In some aspects of the system, the random nucleotide sequence of the primer and/or double-stranded polynucleotide adapters used in the methods of the system consists of 3 to 30 nucleotides, or alternatively 3 to 20, or alternatively 3 to 15 nucleotides, or alternatively 6 to 15 nucleotides, or alternatively 6 to 9 nucleotides, or any numerical nucleotide length therein. For example, the random nucleotide sequence can be 3, 4, 5, 6, 7, 8, 9, 10, 11, 12, 13, 14, 15, 16, 17, 18, 19, 20, 21, 22, 23, 24, 25, 26, 27, 28, 29 or 30 nucleotides in length. It is also understood that one of ordinary skill in the art would be able to readily select the length of the random nucleotide sequence used in the primer and/or double-stranded polynucleotide adapter depending on the desired RNA molecule being selected or made into a cDNA library.

The system also provides that mixtures of primers and/or mixtures of double-stranded polynucleotide adapters having various lengths of the random nucleotide sequence can be used in the claimed methods. For example, when a plurality of primers are used to generate the cDNA complement of the RNA molecule (FIGS. 1A, 1B, 2A and 2B), the primers can have all the same length of random nucleotides or various lengths as disclosed herein. Additionally, when both a primer and a double-stranded adapter is used in a method of the system, the length of the random nucleotide sequence for each type of molecule can be independently selected to have the same or different lengths.

In some aspects, the system provides the double-stranded polynucleotide adapter, such as the polynucleotide used in Method A, includes a 3' overhang that hybridizes to the cDNA generated by reverse transcription. In some aspects, this 3' overhang can include a 3' block as disclosed herein. The presence of the 3' block on the overhang can inhibit or prevent improper ligation products from being formed and/or undesirable primer extension products during the methods of the system. Inhibiting or preventing the formation of these products can increase the reliability of the cDNA produced by the methods of the system.

In some aspects of the system, the method can include a step of separating and/or removing the RNA molecule that was used to generate the cDNA molecule during reverse transcription. Methods for removing RNA molecules in a sample are well known in the art and can be readily selected by one of ordinary skill in the art for use in the methods of the system. For example, methods that can be used to remove the RNA from the sample include incubating the cDNA molecules with a ribonuclease (RNase) that catalyzes the degradation of RNA into smaller components. A particularly effective ribonuclease that can be used in the methods of the system is RNase H, a ribonuclease that cleaves the RNA in a DNA/RNA duplex to produce ssDNA. RNase H is a non-specific endonuclease and catalyzes the cleavage of RNA via a hydrolytic mechanism, aided by an enzyme-bound divalent metal ion.

Figure 1B:
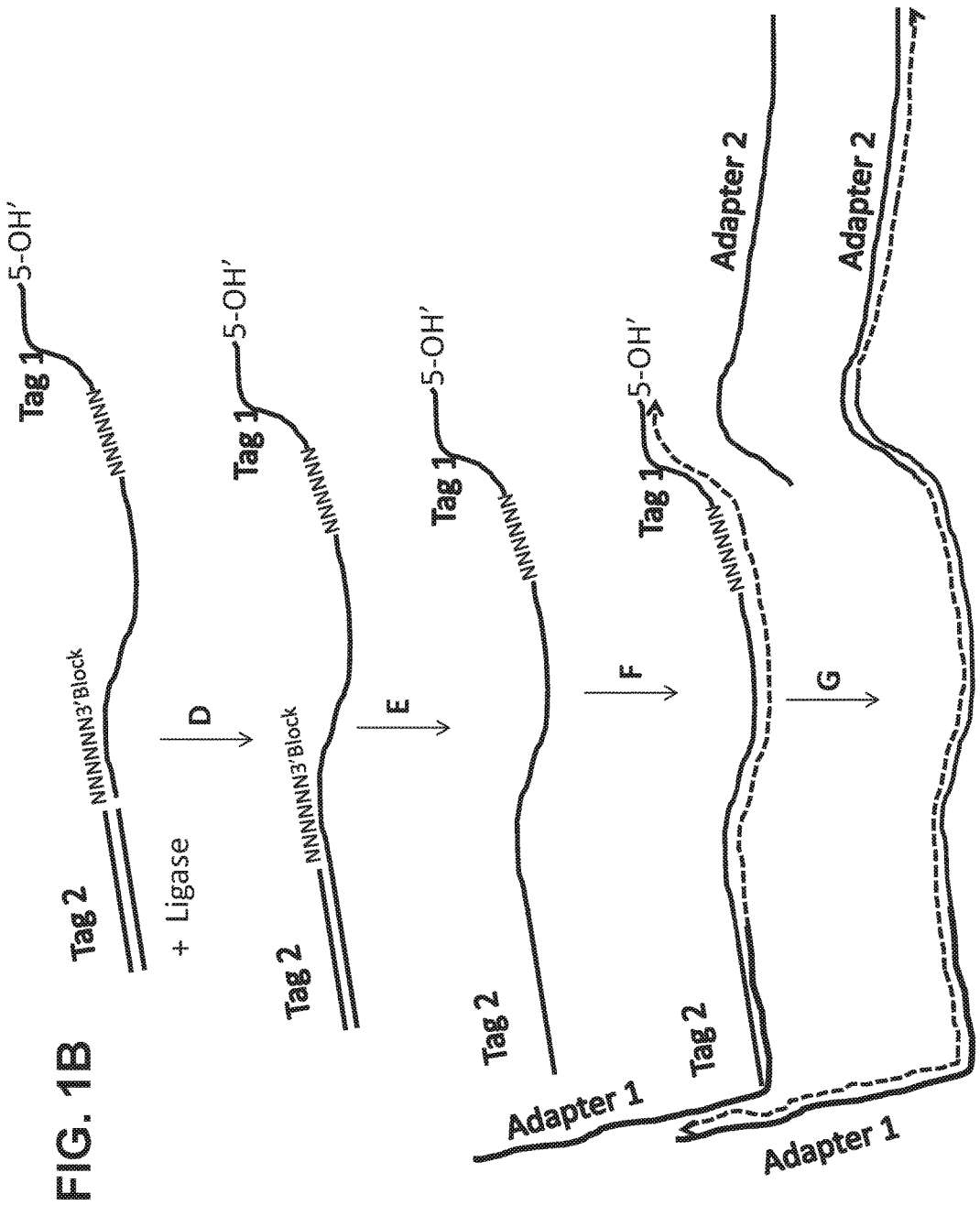

In some aspects of the system, the method includes attaching a polynucleotide to an adjacent polynucleotide, such as attaching the 5' end of the complementary second strand of the double-stranded polynucleotide molecule to the 3' end of the cDNA molecule as disclosed in FIG. 1B and Method A, or attaching the 5' end of the complementary second strand of the double stranded polynucleotide molecules to the 3' end of the cDNA molecules as disclosed in FIG. 2A and Method B. It is understood that methods for attaching adjacent polynucleotides are well known in the art and can be readily selected by one of ordinary skill in the art for use in the methods of the system. For example, attaching adjacent polynucleotides can be done by a ligation reaction includes the linking of two nucleotides by the creation of a phosphodiester bond between the 3' hydroxyl of one nucleotide and the 5' phosphate of another, by a ligase enzyme. There are two types of ligation reactions that commonly referred to as "sticky end" and "blunt end" ligations, depending on the presence or absence of complementary single stranded regions on the two polynucleotides to be joined, in proximity to the ligation location. "Sticky-end" ligations involve the hybridization of complementary single stranded sequences between the two polynucleotides to be joined, prior to the ligation event itself, whereas "blunt end" ligations do not include hybridization of complementary regions because both polynucleotides end at the same base pair.

In some aspects, the methods of the system include hybridization of a polynucleotide to a primer, probe or other polynucleotide of the system. For example, both Methods A and B include the hybridization of a first primer to the RNA molecule (Step A of FIGS. 1A and 2A), or Method A includes hybridizing the 3' overhang region of the double-stranded polynucleotide adapter to the cDNA (FIG. 1B), or both Method A and B may further include hybridizing and/or ligating a second primer or a probe to a nucleotide sequence tag in order to select the cDNA strand of an RNA molecule present in the RNA sample (FIGS. 1B and 2B). It is understood that methods for hybridizing are well known to one of ordinary skill in the art and can be readily selected by one of ordinary skill for use in the methods of the system.

Conditions for hybridization in the present system are generally high stringency conditions as known in the art, although different stringency conditions can be used. Stringency conditions have been described, for example, in Green and Sambrook, (2012) Molecular Cloning: A Laboratory Manual, 4th edition (Cold Spring Harbor Laboratory Press); or the series Ausubel et al. eds., (2012) Current Protocols in Molecular Biology, (John Wiley & Sons, Inc.). High stringency conditions favor increased fidelity in hybridization, whereas reduced stringency permit lower fidelity. Stringent conditions are sequence-dependent and will be different in different circumstances. Longer sequences hybridize specifically at higher temperatures. An extensive guide to the hybridization of nucleic acids is found in Tijssen, "Overview of principles of hybridization and the strategy of nucleic acid assays" in Techniques in Biochemistry and Molecular Biology—Hybridization with Nucleic Acid Probes (1993). Generally, stringent conditions are selected to be about 5-10 C.° lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (i.e., as the target sequences are present in excess, at Tm, 50% of the probes are occupied at equilibrium). Examples of stringent conditions are those in which the salt concentration is less than about 1.0 M sodium ion, typically about 0.01 to 1.0 M sodium ion concentration (or other salts) at pH 7.0 to 8.3 and the temperature at least about 30° C. for short probes (e.g. 10 to 50 nucleotides) and at least about 60° C. for long probes (e.g. greater than 50 nucleotides). Stringent conditions can also be achieved with the addition of helix-destabilizing agents such as formamide. Stringency can be controlled by altering a step parameter that is a thermodynamic variable such as temperature or concentrations of formamide, salt, chaotropic salt, pH, and/or organic solvent. These parameters can also be used to control non-specific binding, as is generally outlined in U.S. Pat. No. 5,681,697. Thus it may be desirable to perform certain steps at higher stringency conditions to reduce non-specific binding.

In some aspects, the methods of the system includes extending a primer or probe that is hybridized to the target polynucleotide. For example, is some aspects, a second primer or probe that is hybridized to the first or second sequence tag is extended. In some aspects, the methods of the system include synthesizing a complementary second stand DNA from cDNA, which can include extending a hybridized polynucleotide molecule such as a probe or primer. In some aspects, synthesizing a complementary second strand DNA molecule includes extending an existing hybridized polynucleotide or in other aspects, hybridizing and extending a separate probe or primer. Methods for extending a primer or probe are well known to one of ordinary skill in the art and can be readily selected by one of ordinary skill for use in the methods of the system. For example, there are a wide variety of suitable extension enzymes, of which polymerases (both RNA and DNA, depending on the composition of the polynucleotide) are useful. Polymerases that can be used in the methods of the system include those that lack strand displacement activity, such that they will be capable of adding only the necessary bases at the end of the primer, without further extending the primer to include nucleotides that are complementary to a targeting domain and thus preventing circularization. Suitable polymerases include, but are not limited to, both DNA and RNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., or Q beta replicase from bacteriophage, also SP6, T3, T4 and T7 RNA polymerases can be used, among others.

Moreover, polymerases that are particularly useful are those that are essentially devoid of a 5' to 3' exonuclease activity, so as to assure that the primer will not be extended past the 5' end of the template. Exemplary enzymes lacking 5' to 3' exonuclease activity include the Klenow fragment of the DNA Polymerase and the Stoffel fragment of DNAPTaq Polymerase. For example, the Stoffel fragment of Taq DNA polymerase lacks 5' to 3' exonuclease activity due to genetic manipulations, which result in the production of a truncated protein lacking the N-terminal 289 amino acids. (See e.g., Lawyer et al., J. Biol. Chem., 264:6427-6437 (1989); and Lawyer et al., PCR Meth. Appl., 2:275-287 (1993)). Analogous mutant polymerases have been generated for polymerases derived from *T. maritima*, Tsps17, TZ05, Tth and Taf.

Other useful polymerases include those that lack a 3' to 5' exonuclease activity, which is commonly referred to as a proof-reading activity, and which removes bases which are mismatched at the 3' end of a primer-template duplex. Although the presence of 3' to 5' exonuclease activity provides increased fidelity in the strand synthesized, the 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of a primer used in a primer extension process can be critical as it is from this terminus that extension of the nascent strand begins. Degradation of the 3' end leads to a shortened primer which in turn results in a loss of specificity in the priming reaction (i.e., the shorter the primer the more likely it becomes that spurious or non-specific priming will occur).

Still further useful polymerases are thermostable polymerases. For the purposes of some embodiments, a heat resistant enzyme is defined as any enzyme that retains most of its activity after one hour at 40° C. under optimal conditions. Examples of thermostable polymerase which lack both 5' to 3' exonuclease and 3' to 5' exonuclease include Stoffel fragment of Taq DNA polymerase. This polymerase lacks the 5' to 3' exonuclease activity due to genetic manipulation and no 3' to 5' activity is present as Taq polymerase is naturally lacking in 3' to 5' exonuclease activity. Tth DNA polymerase is derived from *Thermus thermophilus*, and is available from Epicentre Technologies, Molecular Biology Resource Inc., or Perkin-Elmer Corp. Other useful DNA polymerases which lack 3' exonuclease activity include a Vent® (exo-), available from New England Biolabs, Inc., (purified from strains of *E. coli* that carry a DNA polymerase gene from the archaebacterium *Thermococcus litoralis*), and Hot Tub DNA polymerase derived from *Thermus flavus* and available from Amersham Corporation.

Other suitable enzymes for the methods disclosed herein are thermostable and deprived of 5' to 3' exonuclease activity and of 3' to 5' exonuclease activity include AmpliTaq Gold. Other DNA polymerases, which are at least substantially equivalent may be used like other N-terminally truncated *Thermus aquaticus* (Taq) DNA polymerase I. the polymerase named KlenTaq I and KlenTaq LA are quite suitable for that purpose. Of course, any other polymerase having these characteristics can also be used according to the system. Other polymerases include Bst polymerase, Phusion polymerase, Vent polymerase, T7 polymerase, and 9° N polymerase.

Still further, other suitable enzymes for extending the primers are ligases used in combination with as little as a single nucleic acid residue or a polynucleotide that hybridizes to the template nucleic acid sequence. DNA ligase catalyzes the ligation of the 3' end of a DNA fragment to the 5' end of a directly adjacent DNA fragment. Any number of ligases can be used in the methods disclosed herein. For example, T4 DNA ligase, *E. coli* DNA ligase, and Taq DNA ligase are commonly used and are well characterized ligases suitable for the methods of the system disclosed herein.

Amplification and/or extension may also be performed using a mixture that contains enzymes such as a helicase, recombinase, and/or RNase.

In some aspects of the system, the method provides extending a primer or probe that includes incorporation of a detectable label into the extension product. Methods of incorporating a detectable label either during extension or after extension are well known in the art and can be readily chosen by one of ordinary skill for use in the methods of the system. For example, the method can include polymerase-catalyzed incorporation of deoxynucleoside monophosphates (dNMPs) into a primer at each template site, wherein a pyrophosphate is released whenever DNA polymerase adds one of the four dNTPs onto a primer 3' end. The released pyrophosphate can be detected using a chemiluminescent based detection of the pyrophosphate as described in Hyman E. D. (1988, Analytical Biochemistry 174:423 436) and U.S. Pat. No. 4,971,903. The detection of the pyrophosphate can also be done using ATP sulfurylase to reconvert the pyrophosphate to ATP, which can be detected by a luciferase chemiluminescent reaction as described in U.S. Pat. No. 4,971,903 and Ronaghi (1998, Science 281:363 365). Other methods known in the art use dNTPs tagged at the 3' OH position with four different colored fluorescent tags, one for each of the four nucleotides is described in Metzger, M. L., et al. (1994, Nucleic Acids Research 22:4259 4267). In this approach, the primer/template duplex is contacted with all four dNTPs simultaneously. Incorporation of a 3' tagged NMP blocks further chain extension. The excess and unreacted dNTPs are flushed away and the incorporated nucleotide is identified by the color of the incorporated fluorescent tag. Another well known method is based on detection of DNA polymerase catalyzed incorporation of each of the four nucleotide types, when deoxynucleoside triphosphates (dNTP's) are supplied individually and serially to a DNA primer/template system. See, U.S. Pat. No. 7,037,687. Another non-limiting example of methods for incorporation of a detectable label into an extension product useful in the methods of the system include the sequential incorporation of complementary nucleotides, wherein the nucleotides each have a base that is linked to a detectable label via a cleavable linker, such as an azido group or an azide moiety, as described in U.S. Pat. Nos. 7,414,166, 7,427,673, 7,772,384, 7,795,424, 8,084,590 and 8,158,346. As described therein, the nucleotides can have a sugar moiety that includes a protecting group attached via the 2' or 3' oxygen atom, and wherein the identity of each nucleotide incorporated is determined by detection of the label linked to the base, and subsequent removal of the label and the protecting group under a single set of conditions.

In some aspects, the methods of the system can include using a probe or primer that is immobilized to a solid support for detection and/or amplification of a cDNA product of the system. Moreover, selecting a particular strand of an RNA molecule and/or creating a cDNA library of the system can include amplifying the cDNA molecule by the nucleotide sequence tags incorporated by the methods of the system.

Amplification and/or use of an immobilized probe or primer can facilitate identification and analysis of the cDNA products generated by the methods of the system. For example, in one aspect of the system a multiplex amplification reaction such a bridge amplification can be used to amplify the cDNA sequences. Such bridge amplification methods are described in WO 98/44151, WO 96/04404, WO 07/010251, and U.S. Pat. No. 5,641,658, U.S. Pat. No. 6,060,288, U.S. Pat. No. 6,090,592, U.S. Pat. No. 6,468,751, U.S. Pat. No. 6,300,070, and U.S. Pat. No. 7,115,400. Briefly, bridge amplification localizes the target and one or more primers within sufficient proximity so that complementary sequences hybridize. Following hybridization, the single stranded regions are extended with, for example, a template directed nucleic acid polymerase to modify each molecule to include the sequence of the extension product. Multiple rounds of this extension procedure will result in the synthesis of a population of amplicons. Because the target nucleic acid and the probe or primer is immobilized at a feature and its adjacent surrounding area, the amplicons become highly localized and concentrated at the area of the discrete feature. Moreover, additional methods using immobilized primers for amplification and/or detection of polynucleotides are well known in the art. See, for example, U.S. Pat. Nos. 7,960,120, 7,972,820, 7,985,565, 8,143,008, and 8,192,930.

In some aspects of the system, the method can include phosphorylation and/or dephosphorylation of a polynucleotide used by or generated in the methods of the system. For example, in Method B as described herein, the RNA molecule can be dephosphorylated prior to the ligation of double-stranded polynucleotide adapter in order to inhibit the subsequent ligation of the RNA molecule to the adapter. Alternatively, phosphorylated polynucleotides can be used to facilitate ligation. For example, in Method A or B as described herein, ligation of the double-stranded adapter to the cDNA is facilitated by the use of a 5' phosphorylated polynucleotide.

Methods for phosphorylating or dephosphorylating a polynucleotide are well known in the art and can be readily chosen by one of ordinary skill for use in the methods of the system. For example, 5' termini of RNA molecules can be dephosphorylated by reacting the molecules with Calf intestinal phosphatase (CIP) or bacterial alkaline phosphatase (BAP). Organic extraction followed by ethanol precipitation can be used to inactivate these enzymes. However, both enzymes can be difficult to inactivate, which can result in residual phosphatase activity. Alternatively, heat-labile enzymes, such as HK Phosphatase, can be used in dephosphorylating RNA. Since HK Phosphatase is completely and irreversibly inactivated by heating at 70° C. for 15 min, an organic extraction step is not required. A non-limiting example of a method for phosphorylating a polynucleotide include reacting a polynucleotide with T4 polynucleotide kinase. T4 polynucleotide kinase catalyzes the transfer and exchange of Pi from the γ position of ATP to the 5' terminus of polynucleotides (double- and single-stranded DNA and RNA). Additionally, the T4 polynucleotide kinase also catalyzes the removal of 3'-phosphoryl groups from 3'-phosphoryl polynucleotides, deoxynucleoside 3'-monophosphates and deoxynucleoside 3'-diphosphates.

In some aspects, the methods of the system can include nucleic acid sequencing and/or labeling of an amplicon. Such methods for detection are well known in the art. Suitable amplification methods include both target amplification and signal amplification. Target amplification involves the amplification (i.e. replication) of the target sequence, i.e. cDNA to be selected, resulting in a significant increase in the number of the molecules. Amplification strategies include but are not limited to the polymerase chain reaction (PCR) as is generally well know in the art, strand displacement amplification (SDA) as generally described in Walker et al., in Molecular Methods for Virus Detection, Academic Press, Inc., 1995, and U.S. Pat. No. 5,455,166 and U.S. Pat. No. 5,130,238, and nucleic acid sequence based amplification (NASBA) as generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996.

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), invasive cleavage techniques such as Invader™ technology, Q-Beta replicase (QβR) technology, and the use of "amplification probes" such as "branched DNA" that result in multiple label probes binding to a single target sequence.

All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Accordingly, use of any one of these or any other well know method of amplification of the products of the methods of the system can be used in selecting a cDNA strand.

As would be appreciated by one of ordinary skill, in addition to the methods disclosed herein, the practice of the present system can employ conventional techniques of molecular biology, microbiology, cell biology and recombinant DNA, which are well within the skill of the art. See, for example, Green and Sambrook, (2012) Molecular Cloning: A Laboratory Manual, 4th edition (Cold Spring Harbor Laboratory Press); the series Ausubel et al. eds., (2012) Current Protocols in Molecular Biology, (John Wiley & Sons, Inc.); the series Methods in Enzymology (Academic Press, Inc., N.Y.); and Rio et al, (2010) RNA: A Laboratory Manual, Cold Spring Harbor Laboratory.

It is understood that modifications which do not substantially affect the activity of the various embodiments of this invention are also provided within the definition of the invention provided herein. Accordingly, the following example is intended to illustrate but not limit the present invention.

Example I

Unbiased Stranded RNA Library Preparation

In order to create a stranded or directional RNA library, different sequences that hybridize to the 5' and 3' ends of the RNA sequence are preferred. This can be done by directly ligating sequences onto RNA fragments as described in the TruSeq® smRNA kit (Illumina, Inc., San Diego, Calif.). However, direct ligation can result in some bias due to the ligation efficiency and formation of adapter dimers. Alternatively, long forked adapters and incorporation of dUTP during $2^{nd}$ strand cDNA synthesis can be used, which works well because the second cDNA strand is inert during polymerase chain reaction when used in conjunction with high fidelity polymerases, such as Phusion®. However, the forked adapter protocol includes many steps, such as requiring 2nd strand cDNA synthesis, and at least 2 additional purification steps that result in loss of the cDNA because no purification process has 100% recovery. Moreover, the ligation efficiency of these adapters is low, which is most likely due to their secondary structure and long length. The methods described herein do not suffer from these limitations.

The ScriptSeg™ mRNA-Seq Library Preparation Kit (EpiCentre, Madison, Wis.) uses tailed random hexamers to prime cDNA synthesis by putting a unique sequence tag (Tag 1) on the 5' end of the cDNA and the addition of a unique sequence to the 3' end by a terminal tagging oligonucleotide (TTO). The TTO has a random hexamer sequence on the 3' end and a different 5' sequence (Tag 2), but the 3' end is blocked. When the TTO is annealed to the end of the cDNA and the 3' end of the cDNA is extended, Tag 2 is copied. Thus, the resulting cDNA has two different tags. However, this method can have bias due the inefficiency of the terminal tagging process. TTO can anneal all along the cDNA sequences and not just at the end of the mRNA. To obtain a high amount of TTO at the ends, a very large amount of TTO is required.

Described herein are two methods for making stranded RNA libraries that result in a less biased (or bias free) cDNA library for analysis. These methods (termed Method A and Method B) involve ligation of a double-stranded polynucleotide adapter to one end of a tagged cDNA strand. The experiment outlined below can be used to test the quantitative and qualitative results of these methods.

Briefly, both Methods A and B convert RNA to cDNA. The RNA can be mRNA purified with oligo dT beads, rRNA-depleted RNA purified with Ribo-Zero technology, or any other suitable RNA preparation. The cDNA synthesis is primed using a tagged (Tag 1) random primer with X number of nucleotides ($N_x$) followed by reverse transcription (FIGS. 1A and 2A, Step A). The Tag 1 sequence can be the same sequence or the complement of a sequencing primer. For example, in the experiment described below, this Tag 1 sequence could be Illumina SBS3 sequence (Read 1 primer—5'ACACTCTTTCCCTACACGACGCTCTTC-CGATCT3'—SEQ ID NO: 1).

After cDNA synthesis is complete, the RNA can be removed by RNase H digestion or incubation at high temperatures or left intact. The second tag (Tag 2), which is part of a double-stranded DNA molecule, is then ligated to the cDNA (FIGS. 1B, Step D, and 2A, Step C). The sequence of this tag can be, for example, the same as an Illumina SBS491 sequencing primer (Read 2 primer—5'CGGTCTCGGCAT-TCCTGCTGAACCGCTCTTCCGATCT3'—SEQ ID NO: 2).

In Method A, the double-stranded tag contains a 3' overhang of randomized bases of X length ($N_x$) that is blocked on the 3' end (FIG. 1A, Step C). In Method B, the double-stranded tag is blunt ended (FIG. 2A, Step C). In both cases, the complementary SBS491 strand (SBS491') has a phosphate group on the 5' end of the sequence. In the case of Method A, the random hexamer anchors the Tag 2 on the 3' ends of the cDNA and facilitate ligation of the SBS491' strand to the cDNA strand. In the case of Method B, the double-stranded DNA containing Tag 2 is blunt end ligated to the duplex RNA/cDNA complex, such that the only ligation of the SBS491' strand to the cDNA strand is allowed (the RNA will not ligate to the DNA Tag 2 when most DNA ligases are used).

Method A continues with removal of the SBS491 strand (FIG. 1B, Step E) and conversion of the single-stranded cDNA into double-stranded cDNA product by hybridization of the cDNA strand to an adapter that can hybridize to the SB 5491' Tag 2 sequence followed by extension of the adapter (FIG. 1B, Step F). For Method B, the cDNA is converted into the double-stranded form by removing the unligated RNA and SBS491 strand of the Tag 2 sequence, followed by hybridizing of the cDNA strand to an adapter that can hybridize to the SBS491' Tag 2 sequence. Extension of the SBS491' strand will then convert the single stranded cDNA into double-stranded cDNA product. Extension of the adapter can be done using a polymerase having RNase H activity, and/or separate enzymatic cleavage of the RNA strand or incubation at high temperatures can also be used (FIG. 2B, Step D).

In both Methods A and B, the double-stranded cDNA with Tag 1 on the 5' end and Tag 2 on the 3' end can be used as a template for PCR using adapter arms containing the appropriate primer sequences (FIG. 1B, Step G; FIG. 2B, Step E). In the experiment outlined below, the adapters and PCR reagents are used from the TruSeq® Custom Amplicon kit.

Experiment Outline

RNA Purification and Fragmentation.

Sixteen replicates of 100 ng of total Universal Human Reference (UHR) RNA (Agilent, CA) is further purified to remove the rRNA by purification of mRNA. Universal Human Reference RNA is a complex pool of RNA from different cells and tissues, and is the industry standard for complex RNA pool. The mRNA is purified using the TruSeq® Stranded mRNA Kit (Illumina, Inc., San Diego, Calif.) following the manufacture protocol for "Purify and Fragment mRNA" (User Guide (PN 15031047)). However, instead of using the Fragment, Prime, Finish reagent (FPF), a new reagent will be used. The new reagent will contain the Tag 1 random hexamer sequence in the following formulation: 1× First Strand Buffer (5× First Strand Buffer, PN 15012913, diluted 1/5 in RNase-free $H_2O$) and 0.17 mg/mL Tag 1 oligonucleotide (ACACTCTTTCCCTACAC-GACGCTCTTCCGATCT—SEQ ID NO: 3) (TriLink, CA). The RNA is eluted from the beads, fragmented and primed as described by the manufacturer by heating to 94° C. for 8 min. Following the RNA purification and fragmentation steps the first strand is synthesized.

Synthesize First Strand.

First strand cDNA is synthesized for all 16 replicates following the manufacturers protocol for "Synthesize First Strand cDNA" using the Illumina TruSeq® Stranded mRNA kit (User Guide (PN 15031047)). A master mix of Reverse Transcriptase (in this case, use SuperScript II as recommended in the guide) and First Strand Synthesis ActD Mix (FSA) is made following the protocol. This mix is added to the fragmented and primed RNA following the user guide and incubated as recommended.

RNase H Treatment (Method A, Only).

Eight of the 16 replicates are subjected to RNase H treatment, leaving the other eight samples on ice during this step. 0.5 μL RNase H (PN 15012902) are added into each of the eight samples and mixed. Samples are incubated at 16° C. for 1 hour, and heated to 70° C. for 15 min to inactivate the RNase H.

Ligate Tag 2 to cDNA.

Method A. The eight samples that were treated with RNase H are ligated to a double-stranded, phosphorylated random primer overhang Tag 2 DNA. This oligonucleotide is a 1:1 mix of two different oligonucleotides at 9 μM each in 10 mM Tris-HCL, pH 7 and 10 mM NaCl solution. The sequences of the two oligonucleotides: TCGCGAGTTAAT-GCAACGATCGTCGAAATTCGC 3'Phosphate (SEQ ID NO: 4); and 5'PhosphateGCGAATTTCGACGATCGTTG-CATTAACTCGCGA (SEQ ID NO: 5). The eight samples for Method A are approximately 50.5 μL in volume. T4 DNA ligase, 10× reaction buffer and 25 mM ATP solution (Epicentre (PN LH805H)) are added as follows: 6.5 μL 10× reaction buffer, 1.3 μL ATP, 5 μL double-stranded Tag 2 solution, and 1.7 µL T4 DNA Ligase. Samples are incubated for 10 min at 30° C. followed by 10 min at 65° C.

Method B. The eight samples that were not treated with RNase H are ligated to a double-stranded phosphorylated Tag 2 DNA. This oligonucleotide is a 1:1 mix of two different oligonucleotides at 9 µM each in 10 mM Tris-HCL, pH 7 and 10 mM NaCl solution. The sequences of the two oligonucleotides: TCGCGAGTTAATGCAACGATCGTCGAAATTCGC (SEQ ID NO: 6) and 5'PhosphateGCGAATTTCGACGATCGTTGCATTAACTCGCGA (SEQ ID NO: 5). The eight samples for Method B are approximately 50 µL in volume. T4 DNA ligase, 10× reaction buffer and 25 mM ATP solution (Epicentre (PN LH805H)) are added as follows: 6.5 µL 10× reaction buffer, 1.3 µL ATP, 5 µL double-stranded Tag 2 solution, and 1.7 µL T4 DNA Ligase. Samples are incubated for 1 hr at 16° C. followed by 10 min at 65° C.

Clean Up cDNA.

The cDNA is purified with SPRI bead technology (AMPure XP beads, Agencourt, CA) following the manufacturer's protocol. The DNA is eluted with 20 uL of TE (10 mM Tris-HCl, pH 8, 1 mM EDTA, pH 8).

PCR.

The TruSeq® Custom Amplicon PCR reagents and adapters is used following the manufacturer's protocol (TrueSeq® Custom Amplicon User Guide (PN 15027983)) under the section "PCR Amplification" with the following modifications: bring the purified DNA to 50 mM NaOH be added 5 µL 250 mM NaOH to the 20 µL cDNA from the step above. Use a different indexed adapters for each reaction for 16 total different adapter pairs.

PCR Clean Up.

The PCR products are purified with SPRI bead technology (AMPure XP beads, Agencourt, CA) following the manufacturer's protocol. The DNA is eluted with 30 uL of TE (10 mM Tris-HCl, pH 8, 1 mM EDTA, pH 8).

Determine the Concentration of the Library.

The concentration of the purified libraries is determined using the manufacturer's instructions in the Sequencing Library qPCR Quantification Guide (PN 11322363).

Cluster and Sequence Libraries.

The libraries are normalized to 10 nM concentration (each) and pooled by volume (5 µL of each 10 mM library). This pool at 10 nM total concentration will then be denatured and diluted following the instructions in the TruSeq® Cluster Generation Kit v5 Reagent Preparation Guide For Paired-End Runs. The diluted libraries are then clustered on the cBot (PN SY-301-2002) (same pool in every lane) using the TruSeq® PE Cluster Kit v5-CS-GA kit (PN PE-203-5001). The clustered flowcell is then sequenced on a Genome Analyzer IIx using a paired 75 cycle run using four TruSeq® SBS Kit v5-GA kits (PN FC-104-5001).

Data Analysis.

The data from the sequencing run are then demultiplexed using the index sequences of the adapters and the reads for each of the samples are pooled informatically and analyzed using AutoRNA (ILMN script for Tophat/Cufflinks software). The autoRNA script can be used to analyze the sequencing data for read quality, passing filter cluster numbers, alignment, contamination (rRNA, mtrRNA, adapter dimers, PhiX DNA, etc), and coverage of the transcriptome (3' and 5' coverage, average % CV of coverage of the top 1000 highest expressed transcripts, % of correct strand sequenced in each Read (1 and 2), and % of data from exons, introns, untranslated regions (UTR), and untranscribed sequence).

Figure 3:
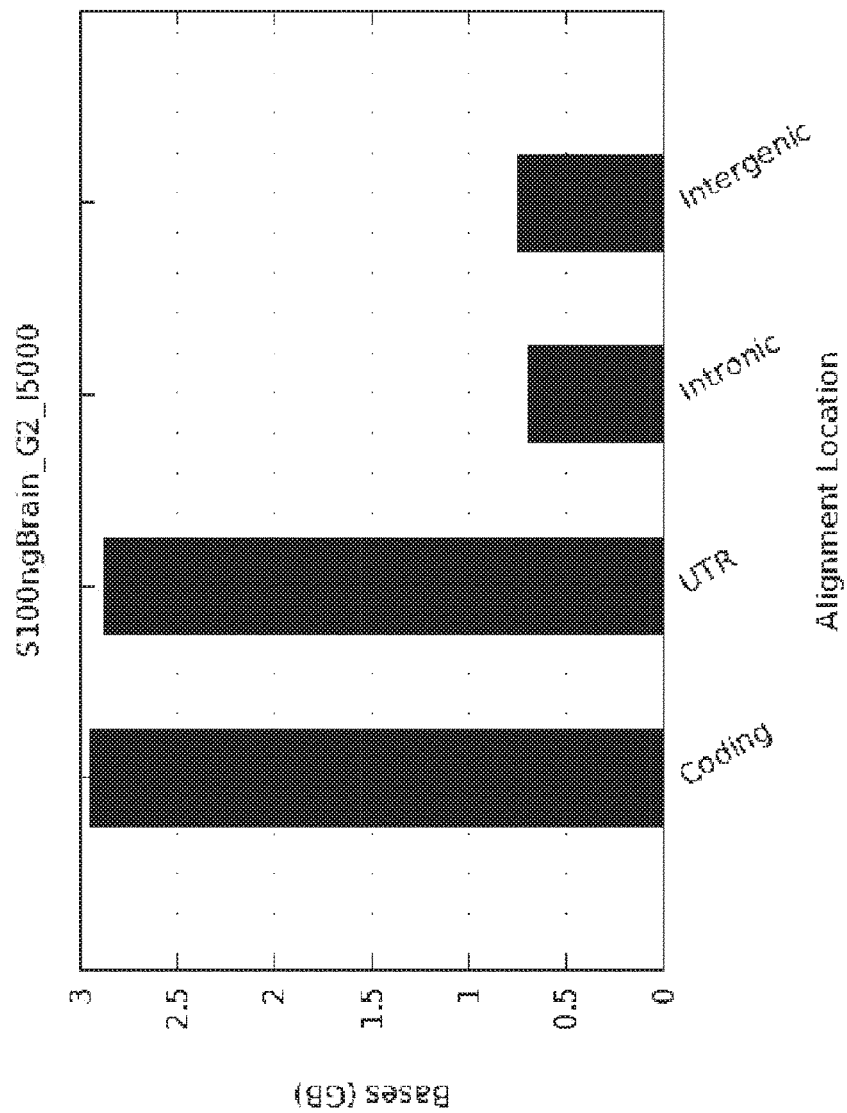
FIG. 3 shows a histogram of biased cDNA generated from a 100 ng sample of brain RNA using TruSeq® Stranded mRNA Sample Prep Kit.
Figure 4:
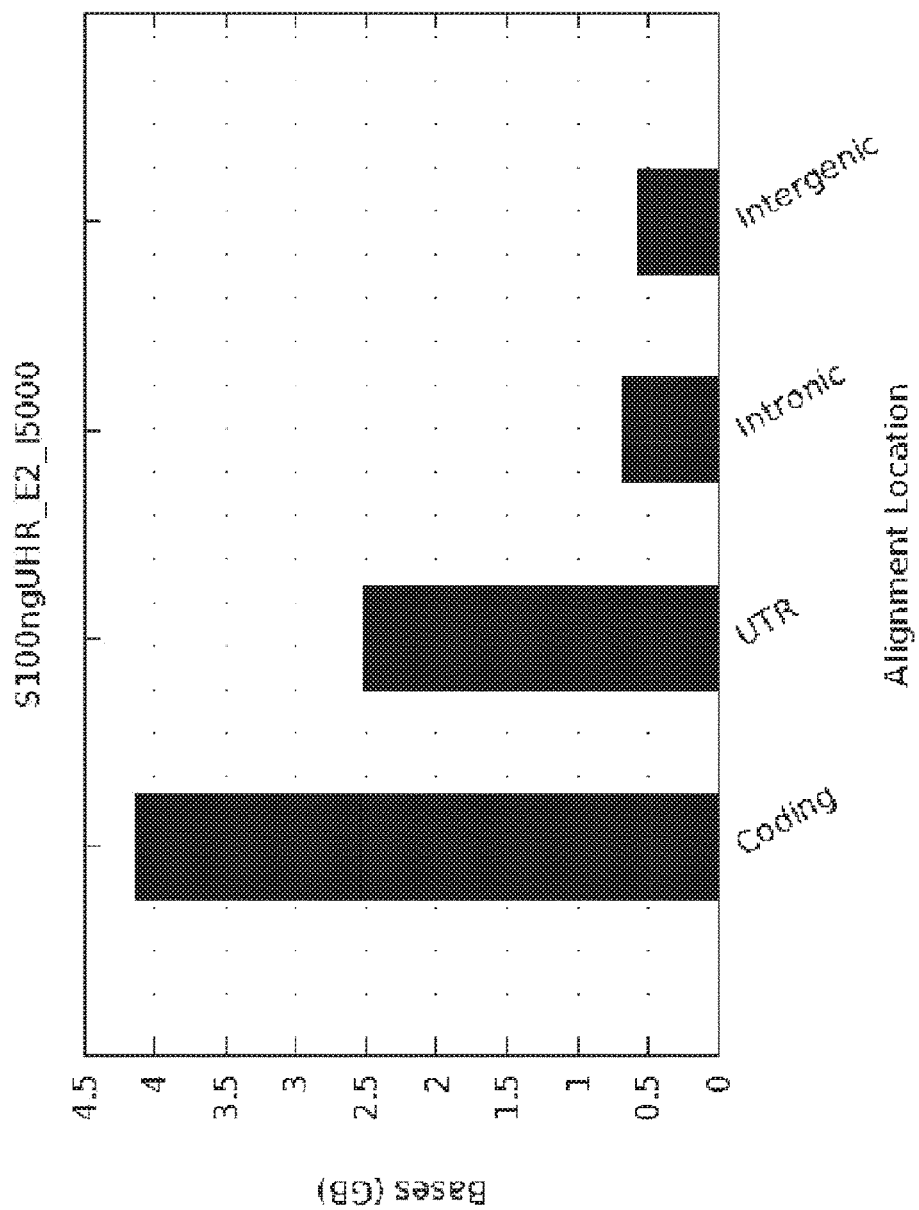
FIG. 4 shows a histogram of biased cDNA generated from a 100 ng sample of the complex Universal Human Reference RNA using TruSeq® Stranded mRNA Sample Prep Kit.

Examples of control data for successful stranded RNA preparations from 100 ng of brain, and UHR RNA using the TruSeq® Stranded mRNA Sample Prep Kit (PN RS-122-2101) is shown in FIG. 3 and FIG. 4. Results from the sequence alignments from brain and UHR replicates showed good replication between replicate samples. For brain RNA, approximately 79.5% of the reads correctly mapped to brain RNA and the correct strand was sequenced and aligned over 98% of the time (approximately 99.4% correctly aligned strand). The UHR RNA also showed a high degree of correctly mapped RNA at approximately 85% of the reads correctly mapped, as well as a high percentage of the correct strand being sequenced and aligned (approximately 99.6%). FIG. 3 and FIG. 4 show that the alignment for both human brain and UHR is specific for the message RNA, as evidenced by the high coverage of exons and UTR sequences. The data from the methods outline above would be comparable to control data, especially for coverage and % of correct strand for each read.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for selecting a particular single-stranded RNA molecule in an RNA sample comprising:
   (a) hybridizing a first primer to the single-stranded RNA molecule in an RNA sample under conditions wherein a complex is formed between the 3' region of the first primer and the single-stranded RNA molecule in the RNA sample, wherein the 3' region of the first primer comprises a first a first random nucleotide sequence and a first nucleotide sequence tag;

(b) extending the first primer complexed to the single-stranded RNA molecule by reverse transcription in the 3' to 5' direction relative to the single-stranded RNA molecule, thereby generating a complementary DNA (cDNA) molecule of the single-stranded RNA molecule;

(c) hybridizing a double stranded polynucleotide molecule comprising a second nucleotide sequence tag to the cDNA molecule, wherein the double stranded polynucleotide molecule comprises a first strand and a complementary second strand, and wherein the first strand comprises a 3' overhang comprising a second random nucleotide sequence, under conditions wherein:
  (i) a complex is formed between the 3' overhang of the double stranded polynucleotide molecule and the 3' region of the cDNA molecule, and
  (ii) the 5' end of the complementary second strand of the double stranded polynucleotide molecule is adjacent to the 3' end of the cDNA molecule;

(d) attaching the 5' end of the complementary second strand of the double stranded polynucleotide molecule to the 3' end of said cDNA molecule forming a covalent bond, thereby leaving the first strand of the double stranded polynucleotide molecule unattached to the cDNA molecule;

(e) removing the unattached strand of the double stranded polynucleotide molecule, thereby forming a single stranded cDNA molecule comprising a first and a second nucleotide sequence tag; and (f) selecting for a particular cDNA strand of the RNA molecule by hybridizing a probe or a second primer to the first or second nucleotide sequence tags.

2. The method of claim 1, wherein the random nucleotide sequence of said first primer consists of 6 to 9 nucleotides.

3. The method of claim 1, wherein the random nucleotide sequence of the double stranded polynucleotide molecule consists of 6 to 9 nucleotides.

4. The method of claim 1, wherein the 3' overhang of the double stranded polynucleotide molecule comprises a 3' block.

5. The method of claim 4, wherein the 3' block is a phosphorylated 3' end of said 3' overhang, an RNA nucleotide, a C3 spacer, or an amine group ($NH_2$).

6. The method of claim 1, wherein step (b) further comprises removing the RNA molecule.

7. The method of claim 6, wherein the removing comprises cleaving the RNA molecule with RNase H.

8. The method of claim 1, wherein step (d) comprises ligating the 5' end of the complementary second strand of the double stranded polynucleotide molecule to the 3' end of the cDNA molecule.

9. The method of claim 1, wherein step (f) comprises hybridizing the second primer to the second nucleotide sequence tag.

10. The method of claim 9, wherein selecting comprises extending the second primer.

11. The method of claim 10, wherein the extension of the second primer comprises incorporation of a detectable label.

12. The method of claim 1, wherein the probe or second primer of step (f) is immobilized to a solid support.

* * * * *

SEQUENCE LISTING

```
<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acactctttc cctacacgac gctcttccga tct                                  33

<210> SEQ ID NO 2
<211> LENGTH: 37
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
cggtctcggc attcctgctg aaccgctctt ccgatct                              37

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, g, unknown or other

<400> SEQUENCE: 3
acactctttc cctacacgac gctcttccga tctnnnnnn                            39

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(39)
<223> OTHER INFORMATION: a, c, t, g, unknown or other
<220> FEATURE:
<223> OTHER INFORMATION: 3'-phosphate

<400> SEQUENCE: 4
tcgcgagtta atgcaacgat cgtcgaaatt cgcnnnnnn                            39

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-phosphate

<400> SEQUENCE: 5
gcgaatttcg acgatcgttg cattaactcg cga                                  33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcgcgagtta atgcaacgat cgtcgaaatt cgc                                  33
```